United States Patent
Carlson et al.

(10) Patent No.: US 10,189,872 B2
(45) Date of Patent: Jan. 29, 2019

(54) CRYSTALLINE FORM OF NICOTINAMIDE RIBOSIDE

(71) Applicant: W. R. Grace & Co.-Conn., Columbia, MD (US)

(72) Inventors: Erik C. Carlson, Albany, OR (US); Jose Osuna, Corvallis, OR (US)

(73) Assignee: W. R. Grace & Co.-Conn, Columbia, MD (US)

( * ) Notice: Subject to any disclaimer, the term of this patent is extended or adjusted under 35 U.S.C. 154(b) by 0 days.

(21) Appl. No.: 15/551,975

(22) PCT Filed: Mar. 3, 2016

(86) PCT No.: PCT/US2016/020537
§ 371 (c)(1),
(2) Date: Aug. 18, 2017

(87) PCT Pub. No.: WO2016/144660
PCT Pub. Date: Sep. 15, 2016

(65) Prior Publication Data
US 2018/0030079 A1    Feb. 1, 2018

Related U.S. Application Data

(60) Provisional application No. 62/130,428, filed on Mar. 9, 2015.

(51) Int. Cl.
| | | |
|---|---|---|
| C07H 1/06 | (2006.01) | |
| A61K 31/706 | (2006.01) | |
| C07H 19/048 | (2006.01) | |

(52) U.S. Cl.
CPC .......... *C07H 19/048* (2013.01); *A61K 31/706* (2013.01); *C07H 1/06* (2013.01); *C07B 2200/13* (2013.01)

(58) Field of Classification Search
None
See application file for complete search history.

(56) References Cited

U.S. PATENT DOCUMENTS

| | | | |
|---|---|---|---|
| 3,708,394 | A | 1/1973 | Nakayama |
| 3,728,111 | A | 4/1973 | Stromblad et al. |
| 7,776,326 | B2 | 8/2010 | Millbrandt |
| 8,106,184 | B2 | 1/2012 | Sauve |
| 8,114,626 | B2 | 2/2012 | Brenner |
| 8,197,807 | B2 | 6/2012 | Brenner |
| 8,217,006 | B2 | 7/2012 | Stamler |
| 8,383,086 | B2 | 2/2013 | Brenner |
| 8,399,489 | B2 | 3/2013 | Basarab |
| 8,481,711 | B2 | 7/2013 | Kaminishi |
| 8,507,251 | B2 | 8/2013 | Greenstein |
| 9,000,147 | B2 | 4/2015 | Sauve |
| 2004/0266723 | A1 | 12/2004 | Otto |
| 2005/0020587 | A1 | 1/2005 | Bailey et al. |
| 2005/0267023 | A1 | 12/2005 | Sinclair et al. |
| 2006/0229265 | A1 | 10/2006 | Milburn et al. |
| 2007/0149466 | A1 | 6/2007 | Milburn |
| 2007/0166296 | A1 | 7/2007 | Burke |
| 2007/0248590 | A1 | 10/2007 | Milne |
| 2008/0146569 | A1 | 6/2008 | Blake et al. |
| 2010/0015072 | A1 | 1/2010 | Polla |
| 2010/0047177 | A1 | 2/2010 | Milbrandt |
| 2010/0279973 | A1 | 11/2010 | Chun et al. |
| 2011/0065662 | A1 | 3/2011 | Rinsch |
| 2011/0306597 | A1 | 12/2011 | Crawforth et al. |
| 2012/0022013 | A1 | 1/2012 | Sinclair |

(Continued)

FOREIGN PATENT DOCUMENTS

| | | |
|---|---|---|
| CA | 2437994 | 5/2011 |
| EP | 0981534 A2 | 3/2006 |
| KR | 1020150050406 | 5/2015 |
| WO | 2006/105440 A2 | 10/2006 |
| WO | WO2007/136744 | 11/2007 |
| WO | WO2011/005289 | 1/2011 |
| WO | WO2013/085555 A3 | 6/2013 |

(Continued)

OTHER PUBLICATIONS

F. Schlenk; Nicotinamide Riboside; Jul. 3, 1943; pp. 93-103.

*Primary Examiner* — Layla D Berry
(74) *Attorney, Agent, or Firm* — Baker & Hostetler LLP

(57) ABSTRACT

Provided are crystalline forms of nicotinamide riboside, including a Form II of nicotinamide riboside chloride: nicotinamide riboside chloride. Also disclosed are pharmaceutical compositions comprising the crystalline Form II of nicotinamide riboside chloride, and methods of producing such pharmaceutical compositions. In other aspects, the present disclosure pertains to methods comprising administering to a subject the crystalline Form II of nicotinamide riboside chloride. The present disclosure also provides methods of preparing the crystalline Form II of nicotinamide riboside chloride. Also provided are a crystalline Form II of nicotinamide riboside chloride that is prepared according to any of the disclosed methods for preparing the crystalline Form II.

24 Claims, 6 Drawing Sheets

(56) References Cited

U.S. PATENT DOCUMENTS

| | | |
|---|---|---|
| 2012/0107888 A1 | 5/2012 | Schmalisch |
| 2012/0172584 A1 | 7/2012 | Sauve et al. |
| 2012/0328526 A1 | 12/2012 | Kristian |
| 2012/0329748 A1 | 12/2012 | Sauve et al. |
| 2013/0059384 A1 | 3/2013 | Tilly |
| 2013/0165398 A1 | 6/2013 | Huber |
| 2014/0045874 A1 | 2/2014 | Tolleth |
| 2014/0065099 A1 | 3/2014 | Alvarez |
| 2014/0221319 A1 | 8/2014 | Sinclair |
| 2014/0256760 A1 | 9/2014 | Tolleth |
| 2014/0364441 A1 | 12/2014 | Wei et al. |
| 2015/0056274 A1 | 2/2015 | Zemel |
| 2015/0118169 A1 | 4/2015 | Hakozaki |
| 2015/0132280 A1 | 5/2015 | Lopez |
| 2015/0133396 A1 | 5/2015 | Sinclair |
| 2015/0174148 A1 | 6/2015 | Brown |
| 2015/0175645 A1 | 6/2015 | Milburn |
| 2015/0297508 A1 | 10/2015 | Andriette |
| 2016/0008329 A1 | 1/2016 | Zemel |
| 2017/0204131 A1 * | 7/2017 | Szczepankiewicz .... C07H 1/00 |

FOREIGN PATENT DOCUMENTS

| | | |
|---|---|---|
| WO | WO2014/059029 | 4/2014 |
| WO | WO2014/111906 | 7/2014 |
| WO | 2015/014722 A1 | 2/2015 |
| WO | WO2015/064988 | 5/2015 |
| WO | WO2015/066382 | 5/2015 |
| WO | WO2015/099842 | 7/2015 |
| WO | WO2015/138969 | 9/2015 |
| WO | WO2015/138986 | 9/2015 |
| WO | WO2016/011360 | 1/2016 |

* cited by examiner

CRYSTALLINE FORM OF NICOTINAMIDE RIBOSIDE

CROSS-REFERENCE TO RELATED APPLICATIONS

This application is a National Stage Application filed under 35 U.S.C. 371 of International Application No. PCT/US2016/020537, filed Mar. 3, 2015, which claims the benefit of U.S. Provisional Patent Application No. 62/130,428, filed on Jul. 24, 2014, the entire contents of both of which are incorporated herein by reference.

TECHNICAL FIELD

The present disclosure relates to crystalline forms of nicotinamide riboside, and in particular, nicotinamide riboside chloride, as well as compositions containing the crystalline form and methods for using the crystalline form.

BACKGROUND

Crystalline forms of useful molecules can have advantageous properties relative to the amorphous form of such molecules. For example, crystal forms are often easier to handle and process, for example, when preparing compositions that include the crystal form. Crystalline forms typically have greater storage stability and are more amenable to purification. The use of a crystalline form of a pharmaceutically useful compound can also improve the performance characteristics of a pharmaceutical product that includes the compound. Obtaining the crystalline form also serves to enlarge the repertoire of materials that formulation scientists have available for formulation optimization, for example by providing a product with different properties, e.g., better processing or handling characteristics, improved dissolution profile, or improved shelf-life.

Nicotinamide riboside (CAS Number 1341-23-7) is a precursor to nicotinamide adenine dinucleotide (NAD) and represents a source of vitamin B3. Recent studies have indicated that novel health benefits may result from ingesting nicotinamide riboside in larger quantities than is found naturally in foods. For example, nicotinamide riboside has been implicated in raising tissue NAD concentrations and in eliciting insulin sensitivity and enhancement of sirtuin functions. See Chi Y, et al., Curr Opin Clin Nutr Metab Care. 2013 November; 16(6):657-61. Its ability to increase NAD production indicates that nicotinamide riboside can also increase mitochondrial health, stimulate mitochondrial function, and induce creation of new mitochondria. Additional studies with nicotinamide riboside in models of Alzheimer's disease have suggested that the molecule is bioavailable to the brain and provides neuroprotective effects, likely by stimulation of brain NAD synthesis. Id. Furthermore, a 2012 study observed that mice on a high-fat diet that was supplemented with nicotinamide riboside gained 60% less weight than mice eating the same high-fat diet without nicotinamide riboside.

Nicotinamide riboside chloride (3-carbamoyl-1-[(2R,3R,4S5R)-3,4-dihydroxy-5-(hydroxymethyl)oxolan-2-yl]-pyrin-1-ylium chloride; also referred to as 1-(β-D-Ribofuranosyl)nicotinamide chloride) is a known salt form of nicotinamide riboside and has the structure depicted below:

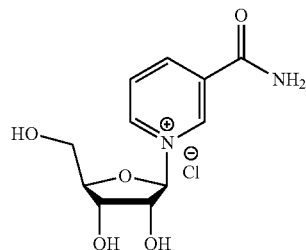

Despite the useful attributes of nicotinamide riboside and its chloride salt, for example, in pharmaceuticals or nutritional supplements, improvements are generally desired.

SUMMARY

The present disclosure pertains to crystalline forms of nicotinamide riboside, including a Form II of nicotinamide riboside chloride

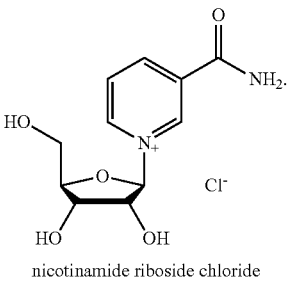

nicotinamide riboside chloride

Also disclosed are pharmaceutical compositions comprising the crystalline Form II of nicotinamide riboside chloride, and methods of producing such pharmaceutical compositions.

In other aspects, the present disclosure pertains to methods comprising administering to a subject the crystalline Form II of nicotinamide riboside chloride.

The present disclosure also provides methods of preparing the crystalline Form II of nicotinamide riboside chloride. Also provided is a crystalline Form II of nicotinamide riboside chloride that is prepared according to any of the disclosed methods for preparing the crystalline Form II.

DETAILED DESCRIPTION OF ILLUSTRATIVE EMBODIMENTS

Figure 1:
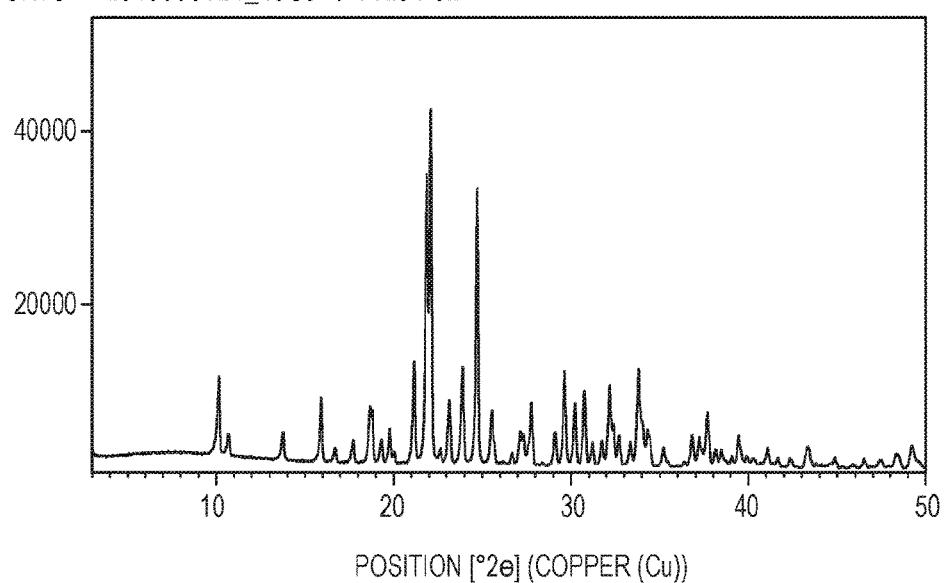
FIG. 1 provides an X-ray powder diffraction pattern for the presently disclosed Form II of crystalline nicotinamide riboside chloride.

The present invention may be understood more readily by reference to the following detailed description taken in connection with the accompanying figures and examples, which form a part this disclosure. It is to be understood that this invention is not limited to the specific products, methods, conditions or parameters described and/or shown herein, and that the terminology used herein is for the purpose of describing particular embodiments by way of example only and is not intended to be limiting of the claimed invention.

The entire disclosures of each patent, patent application, and publication cited or described in this document are hereby incorporated herein by reference.

As employed above and throughout the disclosure, the following terms and abbreviations, unless otherwise indicated, shall be understood to have the following meanings.

In the present disclosure the singular forms "a," "an," and "the" include the plural reference, and reference to a particular numerical value includes at least that particular value, unless the context clearly indicates otherwise. Thus, for example, a reference to "a solvent" is a reference to one or more of such solvents and equivalents thereof known to those skilled in the art, and so forth. Furthermore, when indicating that a certain element "may be" X, Y, or Z, it is not intended by such usage to exclude in all instances other choices for the element.

When values are expressed as approximations, by use of the antecedent "about," it will be understood that the particular value forms another embodiment. As used herein, "about X" (where X is a numerical value) preferably refers to ±10% of the recited value, inclusive. For example, the phrase "about 8" refers to a value of 7.2 to 8.8, inclusive; as another example, the phrase "about 8%" refers to a value of 7.2% to 8.8%, inclusive. Where present, all ranges are inclusive and combinable. For example, when a range of "1 to 5" is recited, the recited range should be construed as including ranges "1 to 4", "1 to 3", "1-2", "1-2 & 4-5", "1-3 & 5", and the like. In addition, when a list of alternatives is positively provided, such a listing can also include embodiments where any of the alternatives may be excluded. For example, when a range of "1 to 5" is described, such a description can support situations whereby any of 1, 2, 3, 4, or 5 are excluded; thus, a recitation of "1 to 5" may support "1 and 3-5, but not 2", or simply "wherein 2 is not included."

As used herein, the terms "treatment" or "therapy" (as well as different word forms thereof) includes preventative (e.g., prophylactic), curative, or palliative treatment. Such preventative, curative, or palliative treatment may be full or partial. For example, complete elimination of unwanted symptoms, or partial elimination of one or more unwanted symptoms would represent "treatment" as contemplated herein.

As employed above and throughout the disclosure the term "effective amount" refers to an amount effective, at dosages, and for periods of time necessary, to achieve the desired result with respect to the treatment of the relevant disorder, condition, or side effect. It will be appreciated that the effective amount of components of the present invention will vary from patient to patient not only with the particular compound, component or composition selected, the route of administration, and the ability of the components to elicit a desired response in the individual, but also with factors such as the disease state or severity of the condition to be alleviated, hormone levels, age, sex, weight of the individual, the state of being of the patient, and the severity of the condition being treated, concurrent medication or special diets then being followed by the particular patient, and other factors which those skilled in the art will recognize, with the appropriate dosage ultimately being at the discretion of the attendant physician. Dosage regimens may be adjusted to provide the improved therapeutic response. An effective amount is also one in which any toxic or detrimental effects of the components are outweighed by the therapeutically beneficial effects. As an example, the compounds useful in the methods of the present invention are administered at a dosage and for a time such that the level of activation and adhesion activity of platelets is reduced as compared to the level of activity before the start of treatment.

"Pharmaceutically acceptable" refers to those compounds, materials, compositions, and/or dosage forms which are, within the scope of sound medical judgment, suitable for contact with the tissues of human beings and animals without excessive toxicity, irritation, allergic response, or other problem complications commensurate with a reasonable benefit/risk ratio.

The amount of solvent used in a process may be referred to as a number of "volumes" or "vol," e.g., a material may be suspended in 5 volumes of a solvent. Those skilled in the art understand this to mean milliliters of the solvent per gram of the material, such that suspending 10 grams of a material in 5 volumes of a solvent means that the solvent is used in an amount of 5 mL of solvent per gram of the material, i.e., 50 mL of solvent.

Provided herein are crystalline forms of nicotinamide riboside chloride. Although nicotinamide riboside and its chloride salt are well known among those of ordinary skill in the art in their amorphous forms and have numerous uses deriving, for example, from the ability of such molecules to increase NAD production, the present disclosure is directed to these molecules in a new crystalline form. Crystalline forms of nicotinamide riboside have advantageous properties, including, for example, improved chemical purity, flowability, solubility, morphology or crystal habit, and/or stability (such as, for example, storage stability, stability to dehydration, stability to polymorphic conversion, low hygroscopicity, and/or low content of residual solvents).

A crystal form may be referred to herein as being characterized by graphical data substantially "as depicted in" a Figure. Such data include, for example, powder X-ray diffractograms and solid state IR spectra. The skilled person will understand that such graphical representations of data may be subject to small variations, e.g., in peak relative intensities and peak positions due to factors such as variations in instrument response and variations in sample concentration and purity, which are well known to the skilled person. Nonetheless, the skilled person would readily be capable of comparing the graphical data in the Figures herein with graphical data generated for an unknown crystal form and confirm whether the two sets of graphical data are characterizing the same crystal form or two different crystal forms.

The present disclosure pertains to crystalline forms of nicotinamide riboside, including a Form II of nicotinamide riboside chloride

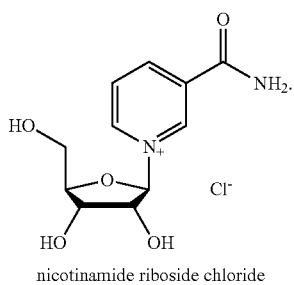

nicotinamide riboside chloride

The crystalline Form II may be characterized by a powder X-ray diffraction pattern having peaks at 21.9, 22.1, and 24.7 degrees two theta±0.2 degrees two theta. The crystalline Form II may also or alternatively be characterized by a powder X-ray diffraction pattern having peaks at 21.2, 21.9, 22.1, 24.7, and 33.8 degrees two theta±0.2 degrees two theta. The crystalline Form II may also or alternatively be characterized by a powder X-ray diffraction pattern having peaks at 21.2, 21.9, 22.1, 23.9, 24.7, 29.6, and 33.8 degrees two theta±0.2 degrees two theta. The crystalline Form II may also or alternatively be characterized by a powder X-ray diffraction pattern having peaks at 10.2, 10.7, 13.8, 21.2, 21.9, 22.1, 23.2, 23.9, 24.7, 29.6, and 33.8 degrees two theta±0.2 degrees two theta.

In other embodiments, the crystalline Form II may be characterized by a powder X-ray diffraction pattern substantially as shown in FIG. 1. The crystalline Form II may also or alternatively be characterized by a powder X-ray diffraction pattern having peaks substantially as provided in Table 1, below, ±0.2 degrees two theta.

TABLE 1

| Peak No. | Pos. [°2Th.] | d-spacing [Å] | Height [cts] | I/Imax [%] |
|---|---|---|---|---|
| 1 | 10.1734 | 8.69516 | 8872.54 | 22 |
| 2 | 10.7297 | 8.24557 | 2372.38 | 6 |
| 3 | 13.7715 | 6.43035 | 3169.12 | 8 |
| 4 | 15.9419 | 5.55947 | 6917.89 | 17 |
| 5 | 16.6967 | 5.30981 | 1563.42 | 4 |
| 6 | 17.7158 | 5.0066 | 2459.58 | 6 |
| 7 | 18.6608 | 4.75513 | 6371.29 | 16 |
| 8 | 18.8034 | 4.71939 | 5490.51 | 14 |
| 9 | 19.3122 | 4.5962 | 2506.58 | 6 |
| 10 | 19.7836 | 4.48773 | 3889.72 | 10 |
| 11 | 20.0386 | 4.43118 | 1145.59 | 3 |
| 12 | 21.1597 | 4.19886 | 11308.49 | 28 |
| 13 | 21.8511 | 4.06755 | 33267.81 | 83 |
| 14 | 22.0897 | 4.02416 | 40217.89 | 100 |
| 15 | 22.6246 | 3.93021 | 1364.78 | 3 |
| 16 | 23.175 | 3.8381 | 6832.75 | 17 |
| 17 | 23.9172 | 3.72065 | 10856.41 | 27 |
| 18 | 24.7373 | 3.59913 | 31585.49 | 79 |
| 19 | 25.5431 | 3.48738 | 6010.22 | 15 |
| 20 | 25.7087 | 3.4653 | 2181.9 | 5 |
| 21 | 26.1736 | 3.4048 | 161.7 | 0 |
| 22 | 26.7038 | 3.33838 | 1130.84 | 3 |
| 23 | 27.1486 | 3.28469 | 3669.91 | 9 |
| 24 | 27.3393 | 3.26221 | 3272.49 | 8 |
| 25 | 27.7904 | 3.21027 | 6906.48 | 17 |
| 26 | 28.36 | 3.14708 | 19.68 | 0 |
| 27 | 29.1148 | 3.06719 | 3478.41 | 9 |
| 28 | 29.6458 | 3.01345 | 10547.46 | 26 |
| 29 | 30.2267 | 2.95685 | 6815.84 | 17 |
| 30 | 30.77 | 2.90587 | 8214.63 | 20 |
| 31 | 31.2086 | 2.86602 | 2303.64 | 6 |
| 32 | 31.7408 | 2.81918 | 2534.77 | 6 |
| 33 | 32.1698 | 2.78255 | 8968.05 | 22 |
| 34 | 32.387 | 2.76438 | 4483.56 | 11 |

TABLE 1-continued

| Peak No. | Pos. [°2Th.] | d-spacing [Å] | Height [cts] | I/Imax [%] |
|---|---|---|---|---|
| 35 | 32.7107 | 2.73776 | 3274.16 | 8 |
| 36 | 33.3382 | 2.68765 | 2487.62 | 6 |
| 37 | 33.8022 | 2.65181 | 10970.51 | 27 |
| 38 | 34.0407 | 2.63378 | 4906.24 | 12 |
| 39 | 34.2927 | 2.61284 | 3948.22 | 10 |
| 40 | 34.4374 | 2.60434 | 3138.89 | 8 |
| 41 | 35.2006 | 2.54961 | 2072.88 | 5 |
| 42 | 36.3793 | 2.46966 | 358.75 | 1 |
| 43 | 36.8234 | 2.44089 | 3401.32 | 8 |
| 44 | 37.2034 | 2.41683 | 3062.55 | 8 |
| 45 | 37.6795 | 2.38738 | 5964.24 | 15 |
| 46 | 38.1272 | 2.36036 | 1617.57 | 4 |
| 47 | 38.4674 | 2.34027 | 1518.92 | 4 |
| 48 | 39.0706 | 2.30552 | 817.46 | 2 |
| 49 | 39.4693 | 2.28126 | 3195.69 | 8 |
| 50 | 39.5912 | 2.28016 | 1727.69 | 4 |
| 51 | 39.8916 | 2.25807 | 807.25 | 2 |
| 52 | 40.3086 | 2.23567 | 574.64 | 1 |
| 53 | 40.3937 | 2.2367 | 505.4 | 1 |
| 54 | 40.6826 | 2.21598 | 236.57 | 1 |
| 55 | 41.1003 | 2.19442 | 1994.57 | 5 |
| 56 | 41.6694 | 2.16575 | 910.04 | 2 |
| 57 | 42.4 | 2.13011 | 853.49 | 2 |
| 58 | 43.2915 | 2.08829 | 2010.71 | 5 |
| 59 | 43.4766 | 2.08499 | 1760.75 | 4 |
| 60 | 43.8176 | 2.06442 | 366.03 | 1 |
| 61 | 44.1054 | 2.05162 | 305.69 | 1 |
| 62 | 44.8767 | 2.01813 | 1102.42 | 3 |
| 63 | 45.0048 | 2.01768 | 407.94 | 1 |

Figure 2:
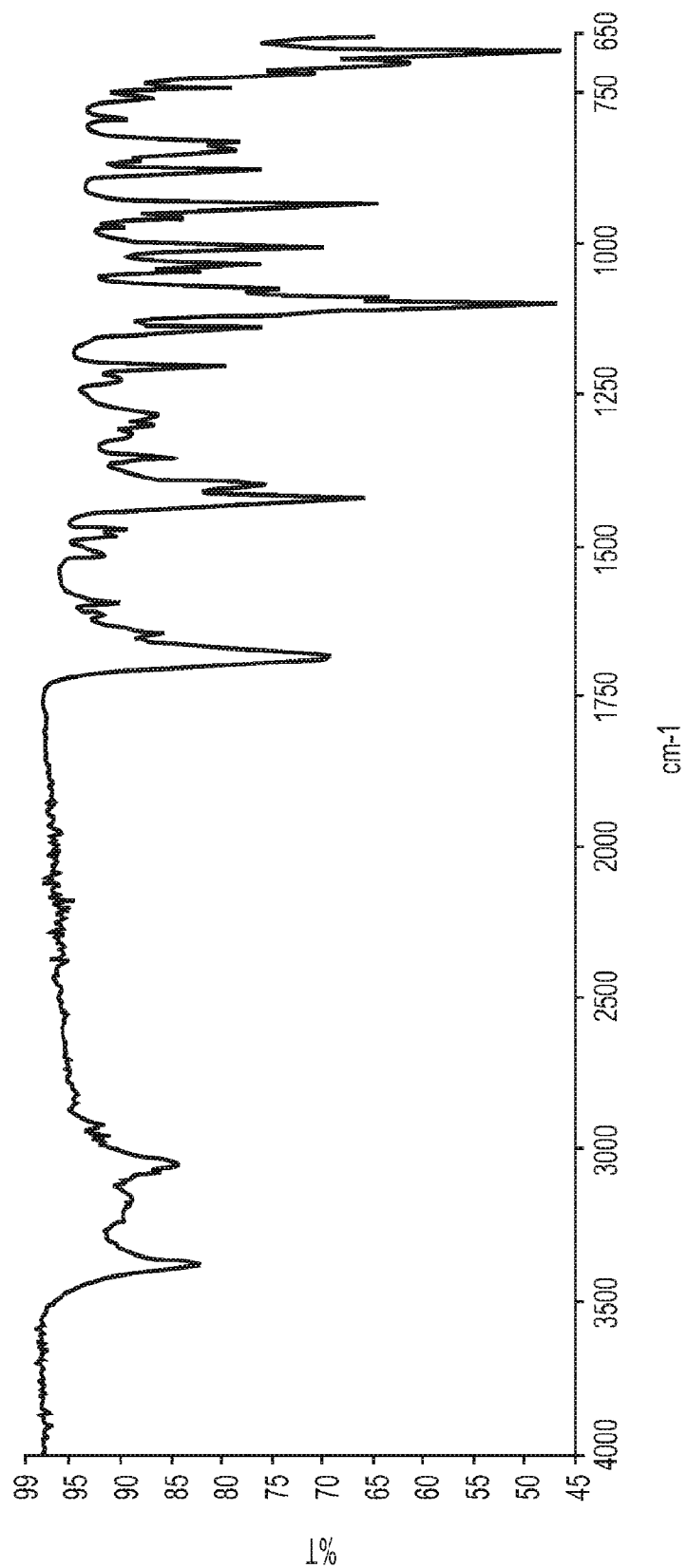
FIG. 2 shows a solid state IR spectrum of the presently disclosed Form II of crystalline nicotinamide riboside chloride.

The crystalline Form II of nicotinamide riboside chloride may also or alternatively be characterized by a solid-state IR spectrum having peaks at 678.3, 695.6, and 1097.5 cm$^{-1}$±0.2 cm$^{-1}$. The crystalline Form II of nicotinamide riboside chloride may also or alternatively be characterized by a solid-state IR spectrum having peaks at 678.3, 695.6, 930.1, 1084.7, and 1097.5 cm$^{-1}$±0.2 cm$^{-1}$. The crystalline Form II of nicotinamide riboside chloride may also or alternatively be characterized by a solid-state IR spectrum having peaks at 678.3, 695.6, 930.1, 998.6, 1084.7, 1097.5, and 1412.6 cm$^{-1}$±0.2 cm$^{-1}$. In certain embodiments, the crystalline Form II of nicotinamide riboside chloride may be characterized by a solid-state IR spectrum substantially as shown in FIG. 2. In further embodiments, the crystalline Form II of nicotinamide riboside chloride may be characterized by a solid-state IR spectrum having peaks substantially as provided in Table 2, below, ±0.2 cm$^{-1}$.

TABLE 2

| IR (cm$^{-1}$) |
|---|
| 3368.98 |
| 3151.73 |
| 3041.76 |
| 2160.79 |
| 1678.65 |
| 1637.22 |
| 1583.98 |
| 1501.94 |
| 1463.57 |
| 1412.55 |
| 1390.1 |
| 1343.99 |
| 1289.17 |
| 1271.66 |
| 1215.75 |
| 1195.17 |
| 1132.1 |
| 1097.53 |
| 1084.69 |

TABLE 2-continued

| IR (cm$^{-1}$) |
| --- |
| 1067.89 |
| 1036.88 |
| 1026.24 |
| 998.64 |
| 961.66 |
| 947.86 |
| 930.11 |
| 870.21 |
| 835.91 |
| 823.25 |
| 781.92 |
| 748.14 |
| 730.95 |
| 711.73 |
| 695.56 |
| 678.34 |

In some embodiments, the crystalline Form II of nicotinamide riboside chloride is characterized by a differential scanning calorimetry (DSC) thermogram having an endotherm peak between 126.4° C. and 126.7° C. For example, the crystalline Form II of nicotinamide riboside chloride may be characterized by a DSC thermogram having a peak at about 126.57° C. This feature may also be expressed as representing a melting point, i.e., that the crystalline Form II of nicotinamide riboside chloride may be characterized as having a melting point at about 126.57° C.

Figure 4:
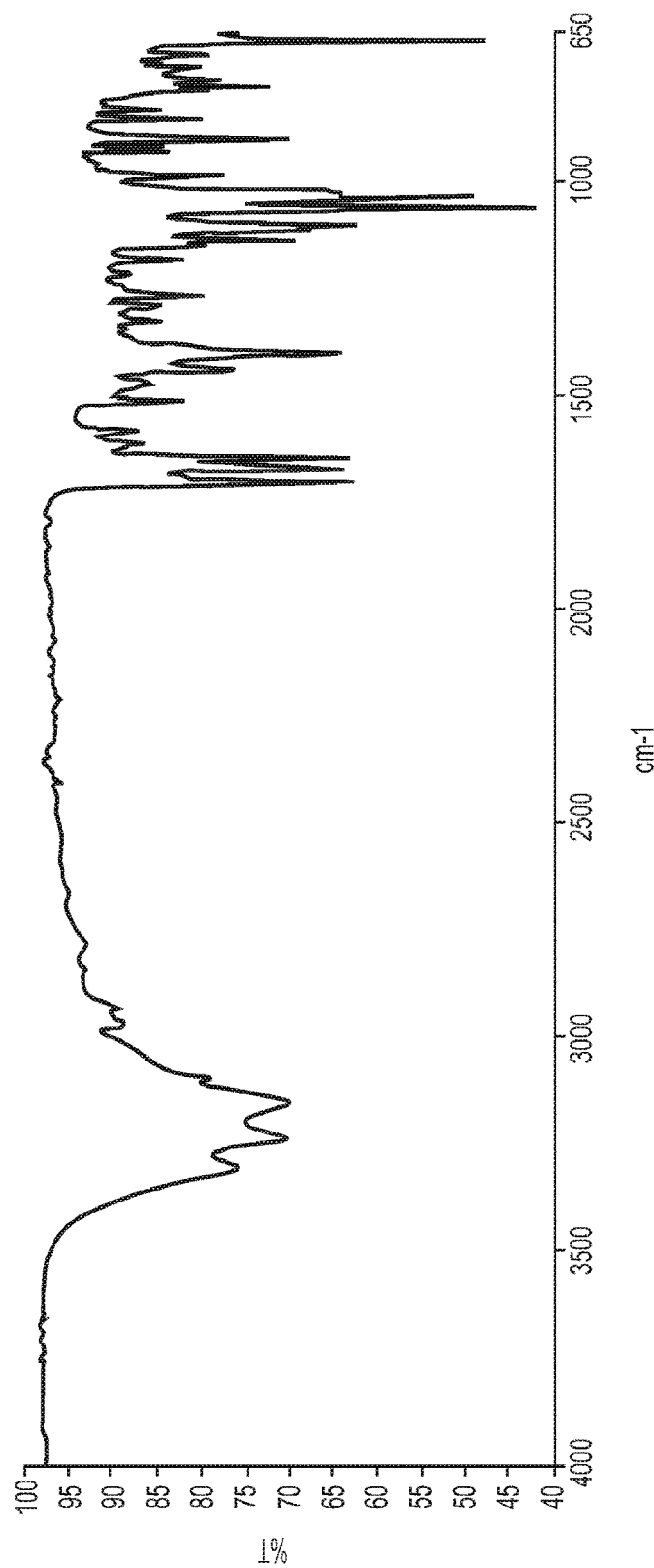
FIG. 4 shows a solid state IR spectrum for the previously described Form I of crystalline nicotinamide riboside chloride.
Figure 5:
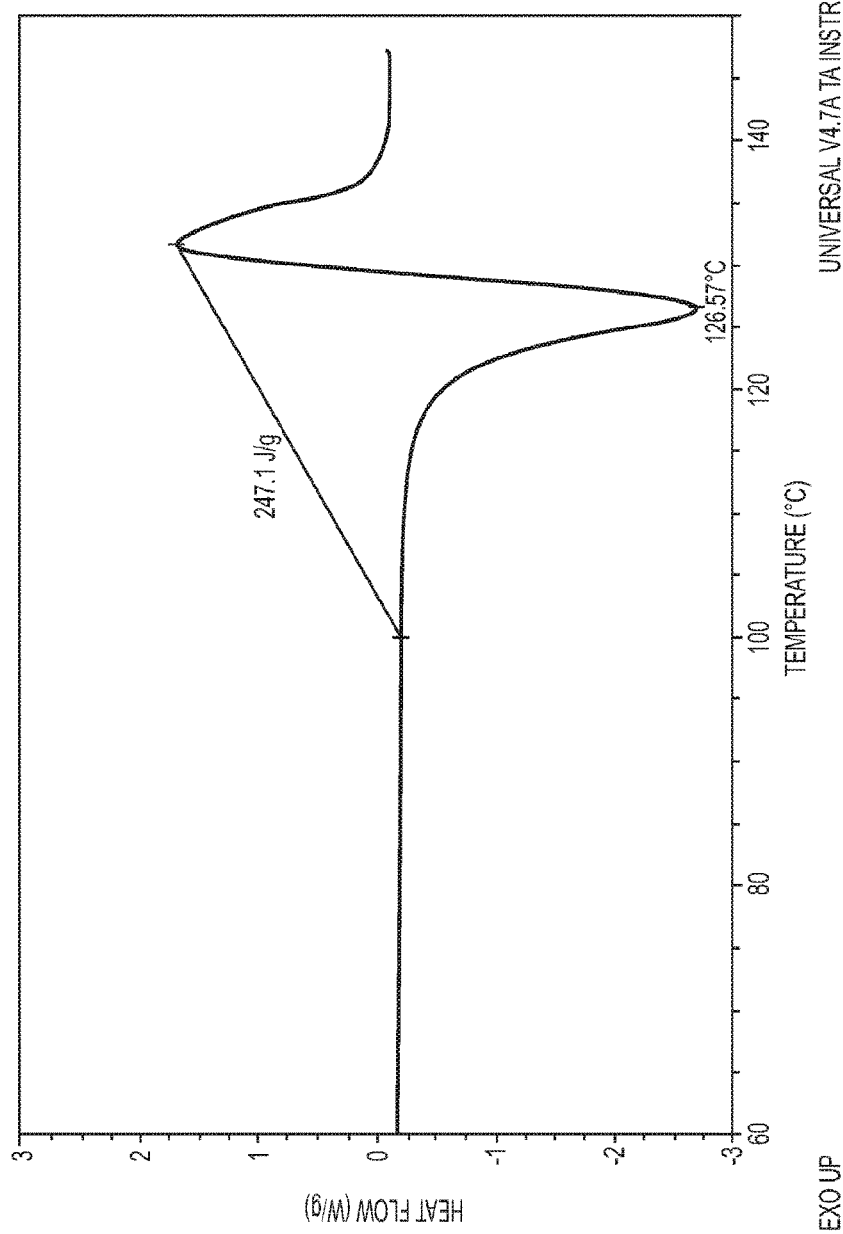
FIG. 5 shows the results of a study that involved measuring the melting point of a sample of the presently disclosed Form II of crystalline nicotinamide riboside chloride using differential scanning calorimetry (DSC).
Figure 6:
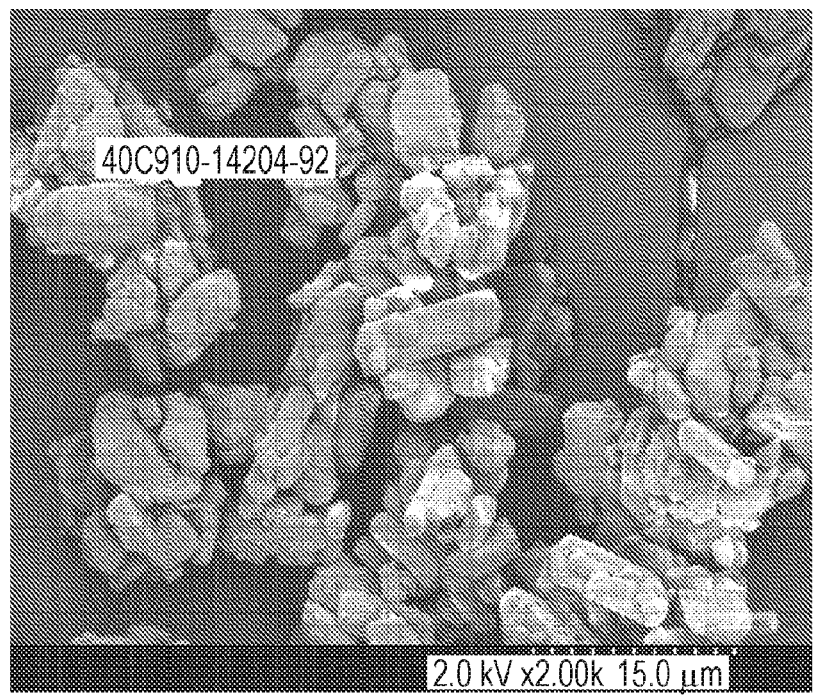
FIG. 6 depicts a Scanning Electron Microscopy (SEM) image of the presently disclosed Form II of crystalline nicotinamide riboside chloride.

The instant crystalline Form II of nicotinamide riboside chloride may be provided in one of several different morphologies. FIG. 4 depicts a Scanning Electron Microscopy (SEM) image of the inventive crystalline nicotinamide riboside chloride in one possible morphology.

In some embodiments, the crystalline Form II of nicotinamide riboside chloride is at least partially hydrated, and in other embodiments, the crystalline Form II of nicotinamide riboside chloride is anhydrous.

The presently disclosed crystalline Form II of nicotinamide riboside chloride represents a different crystalline form of nicotinamide riboside chloride than has been previously disclosed. U.S. Provisional Application No. 62/028,685, filed Jul. 24, 2014, and U.S. Provisional Application No. 62/028,702, filed Jul. 24, 2014 disclose a crystalline Form I of nicotinamide riboside chloride that represents a different crystalline form than the presently disclosed crystalline Form II of nicotinamide riboside chloride. Form I of nicotinamide riboside chloride may be characterized in accordance with the description provided infra in the section of this disclosure titled "Examples".

The present disclosure also pertains to pharmaceutical compositions comprising the crystalline Form II of nicotinamide riboside chloride. The pharmaceutical composition may comprise the crystalline Form II of nicotinamide riboside chloride in any of the embodiments described above, and a pharmaceutically acceptable excipient. The pharmaceutical composition should include a therapeutically effective amount of the crystalline Form II of nicotinamide riboside chloride.

As used herein, the phrase "therapeutically effective amount" refers to the amount of active compound that elicits the biological or medicinal response that is being sought in a tissue, system, animal, individual or human by a researcher, veterinarian, medical doctor or other clinician, which includes one or more of the following:

(1) preventing the disease or condition; for example, preventing a disease, condition or disorder in an individual who may be predisposed to the disease, condition or disorder but does not yet experience or display the pathology or symptomatology of the disease;

(2) inhibiting the disease or condition; for example, inhibiting a disease, condition or disorder in an individual who is experiencing or displaying the pathology or symptomatology of the disease, condition or disorder (i.e., including arresting further development of the pathology and/or symptomatology); and (3) ameliorating the disease or condition; for example, ameliorating a disease, condition or disorder in an individual who is experiencing or displaying the pathology or symptomatology of the disease, condition or disorder (i.e., including reversing the pathology and/or symptomatology).

The present compositions may be formulated for any type of administration. For example, the compositions may be formulated for administration orally, topically, parenterally, enterally, or by inhalation. The crystalline Form II may be formulated for neat administration, or in combination with conventional pharmaceutical carriers, diluents, or excipients, which may be liquid or solid. The applicable solid carrier, diluent, or excipient may function as, among other things, a binder, disintegrant, filler, lubricant, glidant, compression aid, processing aid, color, sweetener, preservative, suspending/dispersing agent, tablet-disintegrating agent, encapsulating material, film former or coating, flavoring agent, or printing ink. Any material used in preparing any dosage unit form is preferably pharmaceutically pure and substantially non-toxic in the amounts employed. In addition, the crystalline Form II may be incorporated into sustained-release preparations and formulations. Administration in this respect includes administration by, inter alia, the following routes: intravenous, intramuscular, subcutaneous, intraocular, intrasynovial, transepithelial including transdermal, ophthalmic, sublingual and buccal; topically including ophthalmic, dermal, ocular, rectal and nasal inhalation via insufflation, aerosol, and rectal systemic.

In powders, the carrier, diluent, or excipient may be a finely divided solid that is in admixture with the finely divided active ingredient. In tablets, the active ingredient is mixed with a carrier, diluent or excipient having the necessary compression properties in suitable proportions and compacted in the shape and size desired. For oral therapeutic administration, the active compound may be incorporated with the carrier, diluent, or excipient and used in the form of ingestible tablets, buccal tablets, troches, capsules, elixirs, suspensions, syrups, wafers, and the like. The amount of active compound(s) in such therapeutically useful compositions is preferably such that a suitable dosage will be obtained.

Liquid carriers, diluents, or excipients may be used in preparing solutions, suspensions, emulsions, syrups, elixirs, and the like. The active ingredient of this invention can be dissolved or suspended in a pharmaceutically acceptable liquid such as water, an organic solvent, a mixture of both, or pharmaceutically acceptable oils or fat. The liquid carrier, excipient, or diluent can contain other suitable pharmaceutical additives such as solubilizers, emulsifiers, buffers, preservatives, sweeteners, flavoring agents, suspending agents, thickening agents, colors, viscosity regulators, stabilizers, or osmo-regulators.

Suitable solid carriers, diluents, and excipients may include, for example, calcium phosphate, silicon dioxide, magnesium stearate, talc, sugars, lactose, dextrin, starch, gelatin, cellulose, methyl cellulose, ethylcellulose, sodium carboxymethyl cellulose, microcrystalline cellulose, polyvinylpyrrolidine, low melting waxes, ion exchange resins, croscarmellose carbon, acacia, pregelatinized starch, crospovidone, HPMC, povidone, titanium dioxide, polycrystalline cellulose, aluminum methahydroxide, agar-agar, tragacanth, or mixtures thereof.

Suitable examples of liquid carriers, diluents and excipients, for example, for oral, topical, or parenteral administration, include water (particularly containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil), or mixtures thereof.

For parenteral administration, the carrier, diluent, or excipient can also be an oily ester such as ethyl oleate and isopropyl myristate. Also contemplated are sterile liquid carriers, diluents, or excipients, which are used in sterile liquid form compositions for parenteral administration. Solutions of the active compounds as free bases or pharmacologically acceptable salts can be prepared in water suitably mixed with a surfactant, such as hydroxypropylcellulose. A dispersion can also be prepared in glycerol, liquid polyethylene glycols, and mixtures thereof and in oils. Under ordinary conditions of storage and use, these preparations may contain a preservative to prevent the growth of microorganisms.

The pharmaceutical forms suitable for injectable use include, for example, sterile aqueous solutions or dispersions and sterile powders for the extemporaneous preparation of sterile injectable solutions or dispersions. In all cases, the form is preferably sterile and fluid to provide easy syringability. It is preferably stable under the conditions of manufacture and storage and is preferably preserved against the contaminating action of microorganisms such as bacteria and fungi. The carrier, diluent, or excipient may be a solvent or dispersion medium containing, for example, water, ethanol, polyol (for example, glycerol, propylene glycol, liquid polyethylene glycol and the like), suitable mixtures thereof, and vegetable oils. The proper fluidity can be maintained, for example, by the use of a coating, such as lecithin, by the maintenance of the required particle size in the case of a dispersion, and by the use of surfactants. The prevention of the action of microorganisms may be achieved by various antibacterial and antifungal agents, for example, parabens, chlorobutanol, phenol, sorbic acid, thimerosal and the like. In many cases, it will be preferable to include isotonic agents, for example, sugars or sodium chloride. Prolonged absorption of the injectable compositions may be achieved by the use of agents delaying absorption, for example, aluminum monostearate and gelatin.

Sterile injectable solutions may be prepared by incorporating the crystalline Form II of nicotinamide riboside chloride in the pharmaceutically appropriate amounts, in the appropriate solvent, with various of the other ingredients enumerated above, as required, followed by filtered sterilization. Generally, dispersions may be prepared by incorporating the sterilized active ingredient into a sterile vehicle which contains the basic dispersion medium and the required other ingredients from those enumerated above. In the case of sterile powders for the preparation of sterile injectable solutions, the preferred methods of preparation may include vacuum drying and freeze drying techniques that yield a powder of the active ingredient or ingredients, plus any additional desired ingredient from the previously sterile-filtered solution thereof.

Thus, the crystalline Form II of nicotinamide riboside chloride may be administered in an effective amount by any of the conventional techniques well-established in the medical field. For example, the administration may be in the amount of about 50 mg/day to about 50,000 mg per day. In some embodiments, the administration may be in the amount of about 250 mg/kg/day. Thus, administration may be in the amount of about 50 mg/day, about 100 mg/day, about 200 mg/day, about 250 mg/day, about 300 mg/day, about 500 mg/day, about 700 mg/day, about 800 mg/day, about 1000 mg/day, about 2000 mg/day, about 4000 mg/day, about 5000 mg/day, about 10,000 mg/day, about 20,000 mg/day, about 30,000 mg/day, about 40,000 mg/day, or about 50,000 mg/day.

Also disclosed are methods of producing such pharmaceutical compositions comprising combining any of the previously disclosed embodiments of the crystalline Form II of nicotinamide riboside chloride with a pharmaceutically acceptable excipient. Any acceptable method of combining an active agent with a pharmaceutically acceptable excipient may be used in accordance with the present methods, and those of ordinary skill in the art can readily appreciate appropriate techniques of combination. In some embodiments, the step of combination may be as simple as adding a desired quantity of the crystalline Form II of nicotinamide riboside chloride to an existing substance, such as a liquid beverage or a powdered beverage mixture. In other embodiments, the step of combination includes any technique that is conventionally used to mix active agents with excipients pursuant to preparing a pharmaceutical dosage form (for example, solid, semi-solid, liquid, or in a form suitable for inhalation), a cosmetic item (such as a powder, cream, lotion, or emollient), or a food item (for example, solid, semi-solid, or liquid).

In other aspects, the present disclosure pertains to methods comprising administering to a subject the crystalline Form II of nicotinamide riboside chloride. The administration of the crystalline Form II of nicotinamide riboside chloride may be by any of the routes described above in connection with the present pharmaceutical compositions. For example, the crystalline Form II of nicotinamide riboside chloride may be administered orally, topically, parenterally, enterally, or by inhalation. In view of the exceptional stability of the presently disclosed crystalline Form II of nicotinamide riboside chloride, the active agent may be used or otherwise prepared for any known route of administration, and any known route of administration may be used pursuant to the present methods. The crystalline Form II of nicotinamide riboside chloride may be administered in combination with a pharmaceutically acceptable excipient.

A subject or patient in whom administration of the therapeutic compound is an effective therapeutic regimen for a disease or disorder is preferably a human, but can be any animal, including a laboratory animal in the context of a clinical trial or screening or activity experiment. Thus, as can be readily appreciated by one of ordinary skill in the art, the methods, compounds and compositions of the present invention are particularly suited to administration to any animal, particularly a mammal, and including, but by no means limited to, humans, domestic animals, such as feline or canine subjects, farm animals, such as but not limited to bovine, equine, caprine, ovine, and porcine subjects, wild animals (whether in the wild or in a zoological garden), research animals, such as mice, rats, rabbits, goats, sheep, pigs, dogs, cats, and the like, avian species, such as chickens, turkeys, songbirds, and the like, i.e., for veterinary medical use.

The present disclosure also provides methods of preparing the crystalline Form II of nicotinamide riboside chloride. The methods may include the steps of forming a mixture comprising nicotinamide riboside chloride and a polar solvent with hydrogen bonding, optionally isolating a wetcake comprising the nicotinamide riboside chloride and optionally a portion of the polar solvent and forming a second mixture comprising the isolated material and an additional quantity of the polar solvent with hydrogen bonding or a different polar solvent with hydrogen bonding, raising the temperature of the mixture or the second mixture, and isolating crystalline nicotinamide riboside chloride from the mixture or the second mixture.

In some embodiments, the polar solvent with hydrogen bonding for forming the mixture and/or the second mixture may be a polar alcohol. Exemplary polar alcohols include methanol, 1-butanol, 2-butanol, t-butyl alcohol, diethylene glycol, ethanol, ethylene glycol, glycerin, 1-propanol, 2-propanol. The polar solvent with hydrogen bonding for forming the solution and/or the second solution may have high water solubility. For example, the polar solvent with hydrogen bonding may be acetone, acetonitrile, diglyme (diethylene glycol dimethyl ether), 1,2-dimethoxy-ethane (DME), dimethyl-formamide (DMF), dimethyl sulfoxide (DMSO), dioxane, hexamethylphosphoramide (HMPA), hexamethylphosphorous triamide (HMPT), N-methyl-2-pyrrolidinone (NMP), or pyridine. The polar solvent with hydrogen bonding may be combined with water.

In some embodiments, the formation of the mixture comprises combining crude nicotinamide riboside chloride (i.e., raw or unrefined nicotinamide riboside chloride) with the polar solvent with hydrogen bonding. In other embodiments, the mixture is formed by combining another form of crystalline nicotinamide riboside chloride with the polar solvent. In such instances, the starting material crystalline nicotinamide riboside chloride may be a Form I of crystalline nicotinamide riboside chloride as described supra and as disclosed in U.S. Provisional Application No. 62/028,685, filed Jul. 24, 2014, may be crystalline nicotinamide riboside chloride as disclosed in U.S. Provisional Application No. 62/028,702, filed Jul. 24, 2014, or may be a mixture of such forms of crystalline nicotinamide riboside chloride.

The formation of the mixture comprising nicotinamide riboside chloride and the polar solvent with hydrogen bonding may occur at a temperature of about 15° C., about 10° C., about 0° C., about −10° C., about −15° C., about −20° C., or about −25° C. In an exemplary embodiment, the temperature ranges from about 15° C. to about −25° C. In other embodiments, the temperature ranges from about −10° C. to about −20° C., or about −5° C. to about −15° C. Following the formation of the mixture comprising nicotinamide riboside chloride and the polar solvent with hydrogen bonding, the solution may be held at a desired temperature, which may be, for example, about 15° C., about 10° C., about 0° C., about −10° C., about −15° C., about −20° C., or about −25° C. The period of time during which the mixture is held at the desired temperature may be about 10 hours, about 12 hours, about 18 hours, about 20 hours, about 24 hours, about 30 hours, about 36 hours, or about 40 hours. In one embodiment, the mixture is held at the desired temperature for about 10 to about 40 hours. The mixture may be subjected to agitation while it is held at the desired temperature.

After forming the mixture comprising nicotinamide riboside chloride and the polar solvent with hydrogen bonding and optionally holding the mixture at a desired temperature, a wetcake comprising the nicotinamide riboside chloride and, in some embodiments, a portion of the polar solvent may optionally be isolated from the mixture. The isolated material may then be combined with an additional quantity of the first polar solvent with hydrogen bonding, with a different polar solvent with hydrogen bonding, or with a combination of the original polar solvent and the different polar solvent, in order to form a second mixture. In one embodiment, the different polar solvent is acetone. The temperature of the second mixture may be about the same as, less than, or more than the temperature of the original mixture comprising nicotinamide riboside chloride and the polar solvent with hydrogen bonding. Preferably, the temperature of the second mixture is about the same as the temperature of the original mixture comprising nicotinamide riboside chloride and the polar solvent with hydrogen bonding.

Whether or not the wetcake is isolated from the first mixture and combined with an additional quantity of the polar solvent with hydrogen bonding or with a different polar solvent, the temperature of the mixture or the second mixture is raised. The temperature may be raised by about 10° C., about 15° C., about 20° C., about 25° C., about 30° C., about 35° C., or about 40° C. For example, the temperature may be raised from a starting temperature of −10° C. to about 20-25° C.

After the temperature is raised or during the increase in temperature, the mixture or the second mixture may be subjected to agitation.

Whether or not the mixture or the second mixture is agitated, water may optionally be added until the mixture or second mixture contains a desired quantity of water relative to the polar solvent or mixture of polar solvents. For example, water may be added until there is about 1%, about 1.5%, about 2%, about 2.5%, about 3%, about 3.5%, about 4%, about 4.5%, about 5%, about 5.5%, or about 6% of water by volume relative to the volume of the polar solvent or mixture of polar solvents.

Whether or not water was added, the mixture or second mixture may be held at the temperature to which it was previously raised for a desired period of time. The period of time during which the mixture or second mixture is held at the raised temperature may range from about 10 to about 40 hours. For example, the temperature may be about 10 hours, about 12 hours, about 18 hours, about 20 hours, about 24 hours, about 30 hours, about 36 hours, or about 40 hours. The mixture or second mixture may be subjected to agitation while it is held at the raised temperature.

Following the period of time at which the mixture or second mixture is held at the raised temperature, solid nicotinamide riboside chloride may then be isolated. The solids are optionally washed, for example, with a polar solvent or mixture of polar solvents, optionally containing water. The solids may also be dried, such as by vacuum drying.

Also disclosed is crystalline Form II of nicotinamide riboside chloride that is prepared according to the above-described process. The crystalline Form II of nicotinamide riboside chloride may be prepared according to any embodiment of the process for forming the crystalline form that is disclosed herein.

The present invention is further defined in the following Examples. It should be understood that these examples, while indicating preferred embodiments of the invention, are given by way of illustration only, and should not be construed as limiting the appended claims. From the above discussion and these examples, one skilled in the art can ascertain the essential characteristics of this invention, and without departing from the spirit and scope thereof, can make various changes and modifications of the invention to adapt it to various usages and conditions.

EXAMPLES

Starting Material—Crude Nicotinamide Riboside

Numerous routes for the synthesis of crude nicotinamide riboside and its chloride salt have been published. Any known route, or any other acceptable route may be used in order to prepare the non-crystalline form of the relevant compound. Exemplary routes for the synthesis of nicotinamide riboside or its chloride salt are disclosed in the following publications: Jarman, et al., J. Chem. Soc. (1969), (2), 199-203 (chloride salt); Yang, et al. J. Med. Chem. 2007, 50, 6458-6461; U.S. Pub. No. 2007/0117765; Franchetti, et al., Bioorg Med Chem Lett. 2004 Sep. 20; 14(18):4655-8; Saunders P P, et al., Cancer Res. 1989 Dec. 1; 49(23):6593-9; Dowden J, et al., Nucleosides Nucleotides Nucleic Acids. 2005; 24(5-7):513-8; Schlenk, F., Archives of Biochemistry (1943), 3, 93-103; Freyne, et al., Carbohydr. Res., 78:235-242 (1980); Tanimori, et al., Bioorg. Med. Chem. Lett., 12:1135-1137 (2002); WO 2010/017374; Davies L C, Nucleosides & Nucleotides 14(3-5), 311-312 1995; Kam B L, et al., Carbohydrate Research, 77 (1979) 275-280; Viscontini M, et al., Volumen XXXIX, Fasciculus VI (1956)—No. 195, 1620-1631. The entire disclosures of each of the references listed above are incorporated herein by reference.

Nicotinamide riboside may be initially synthesized with a different anion than Cl$^-$, for example, triflate or trifluoromethanesulfonate. Following synthesis of this alternative form of nicotinamide riboside, the initial ion may be "exchanged" out, with a chloride anion, or other anion with a higher affinity, taking its place, by means of ion-exchange chromatography. Those of ordinary skill in the art can readily appreciate how to perform ion-exchange chromatography.

Alternatively, amorphous nicotinamide riboside chloride may be acquired from commercial sources.

Preparation of Crystalline Nicotinamide Riboside Chloride Form I

As stated supra, the starting material for preparing Form II of crystalline nicotinamide riboside chloride may be another form of crystalline nicotinamide riboside chloride. For example, the starting material crystalline nicotinamide riboside chloride may be crystalline nicotinamide riboside chloride as disclosed in U.S. Provisional Application No. 62/028,685, filed Jul. 24, 2014, may be crystalline nicotinamide riboside chloride as disclosed in U.S. Provisional Application No. 62/028,702, filed Jul. 24, 2014, or may be a mixture of such forms of crystalline nicotinamide riboside chloride. The above-referenced provisional applications disclose a crystalline Form I of nicotinamide riboside chloride that represents a different crystalline form than the presently disclosed crystalline Form II of nicotinamide riboside chloride.

An exemplary process for forming crystalline Form I of nicotine riboside chloride is as follows. A mixture is formed comprising methanol and crude nicotinamide riboside chloride. Following formation of the solution, the solution is cooled to −10° C. and maintained at that temperature. Over the course of the next 12-24 hours the product begins to crystallize. The rate at which the crystallization occurs can be increased by seeding the solution, for example, using known techniques. Following this period, the mixture is confirmed to be a slurry, and 3 parts (this volume may be varied, for example, from 1-5 parts, depending on the amount of methanol) methyl t-butyl ether is added slowly over ~6-12 hours. The MTBE functions as an anti-solvent in order to push the majority of product out of solution. The reaction mixture is then held at −10° C. for an additional 12 hours. The solids are then filtered and rinsed with MTBE. The resulting solid represents crystalline nicotinamide riboside chloride Form I.

Form I of nicotinamide riboside chloride may be characterized by a powder X-ray diffraction pattern having peaks at 5.1, 15.7, and 21.7 degrees two theta±0.2 degrees two theta. The crystalline Form I may also or alternatively be characterized by a powder X-ray diffraction pattern having peaks at 5.1, 15.7, 21.7, 23.5, and 26.4 degrees two theta±0.2 degrees two theta. The crystalline Form I may also or alternatively be characterized by a powder X-ray diffraction pattern having peaks at 5.1, 15.7, 18.6, 21.7, 23.5, 26.4, and 28.0 degrees two theta±0.2 degrees two theta.

Figure 3:
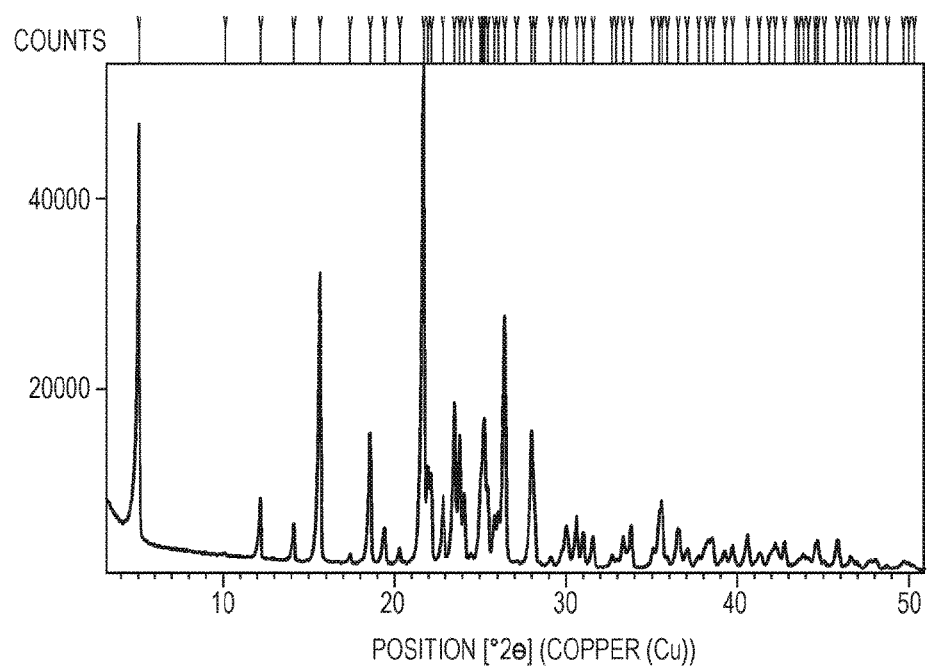
FIG. 3 provides an X-ray powder diffraction pattern for the previously described Form I of crystalline nicotinamide riboside chloride.

In other instances, the crystalline Form I may be characterized by a powder X-ray diffraction pattern substantially as shown in FIG. 3. The crystalline Form I may also or alternatively be characterized by a powder X-ray diffraction pattern having peaks substantially as provided in Table 3, below, ±0.2 degrees two theta.

TABLE 3

| Peak No. | Pos. [°2Th.] | d-spacing [Å] | Height [cts] | I/Imax |
|---|---|---|---|---|
| 1 | 5.0847 | 17.36541 | 29562 | 87% |
| 2 | 10.09 | 8.75955 | 158 | 0% |
| 3 | 12.194 | 7.25232 | 4234 | 12% |
| 4 | 14.141 | 6.25817 | 2433 | 7% |
| 5 | 15.662 | 5.65364 | 19978 | 59% |
| 6 | 17.4 | 5.09227 | 576 | 2% |
| 7 | 18.573 | 4.77348 | 9176 | 27% |
| 8 | 19.415 | 4.56839 | 2563 | 8% |
| 9 | 20.35 | 4.36098 | 831 | 2% |
| 10 | 21.685 | 4.09491 | 33878 | 100% |
| 11 | 21.919 | 4.05175 | 4369 | 13% |
| 12 | 22.148 | 4.01031 | 5971 | 18% |
| 13 | 22.842 | 3.89009 | 4521 | 13% |
| 14 | 23.519 | 3.77954 | 10585 | 31% |
| 15 | 23.825 | 3.73181 | 8674 | 26% |
| 16 | 24.103 | 3.68936 | 4752 | 14% |
| 17 | 24.47 | 3.63519 | 434 | 1% |
| 18 | 25.05 | 3.55221 | 5408 | 16% |
| 19 | 25.149 | 3.53825 | 107 | 0% |
| 20 | 25.244 | 3.52517 | 8758 | 26% |
| 21 | 25.438 | 3.4987 | 4768 | 14% |
| 22 | 25.836 | 3.44564 | 2741 | 8% |
| 23 | 26.035 | 3.41975 | 2662 | 8% |
| 24 | 26.43 | 3.36953 | 18356 | 54% |
| 25 | 28.016 | 3.1823 | 9628 | 28% |
| 26 | 28.164 | 3.16597 | 3910 | 12% |
| 27 | 29.13 | 3.06327 | 552 | 2% |
| 28 | 29.7 | 3.00557 | 799 | 2% |
| 29 | 30.02 | 2.97428 | 2725 | 8% |
| 30 | 30.628 | 2.91661 | 3400 | 10% |
| 31 | 30.996 | 2.88284 | 2421 | 7% |
| 32 | 31.576 | 2.8312 | 2259 | 7% |
| 33 | 32.658 | 2.73983 | 850 | 3% |
| 34 | 32.95 | 2.71631 | 431 | 1% |
| 35 | 33.295 | 2.6888 | 1887 | 6% |
| 36 | 33.8 | 2.64976 | 2964 | 9% |
| 37 | 35.06 | 2.55763 | 1199 | 4% |
| 38 | 35.426 | 2.53179 | 3426 | 10% |
| 39 | 35.586 | 2.5208 | 4384 | 13% |
| 40 | 35.92 | 2.49794 | 500 | 1% |
| 41 | 36.534 | 2.45752 | 2679 | 8% |
| 42 | 37.074 | 2.42298 | 1143 | 3% |
| 43 | 37.616 | 2.3893 | 536 | 2% |
| 44 | 38.13 | 2.35799 | 1057 | 3% |
| 45 | 38.56 | 2.33306 | 1731 | 5% |
| 46 | 39.218 | 2.29527 | 980 | 3% |
| 47 | 39.729 | 2.26696 | 1467 | 4% |
| 48 | 40.624 | 2.21904 | 2257 | 7% |
| 49 | 41.32 | 2.18334 | 890 | 3% |
| 50 | 42.2 | 2.13986 | 1389 | 4% |
| 51 | 42.76 | 2.11298 | 1812 | 5% |
| 52 | 43.79 | 2.06588 | 681 | 2% |

TABLE 3-continued

| Peak No. | Pos. [°2Th.] | d-spacing [Å] | Height [cts] | I/Imax |
|---|---|---|---|---|
| 53 | 44.58 | 2.03105 | 1628 | 5% |
| 54 | 44.68 | 2.02661 | 1483 | 4% |
| 55 | 45.083 | 2.00939 | 363 | 1% |
| 56 | 45.857 | 1.97724 | 2012 | 6% |
| 57 | 46.63 | 1.9463 | 858 | 3% |
| 58 | 46.95 | 1.93366 | 455 | 1% |
| 59 | 47.67 | 1.90628 | 518 | 2% |
| 60 | 48.08 | 1.89074 | 630 | 2% |
| 61 | 49.69 | 1.83344 | 442 | 1% |
| 62 | 49.96 | 1.82422 | 354 | 1% |
| 63 | 50.3 | 1.81235 | 222 | 1% |

The crystalline Form I of nicotinamide riboside chloride may also or alternatively be characterized by a solid-state IR spectrum having peaks at 671.7, 1035.6, and, 1061.8 cm$^{-1}$±0.2 cm$^{-1}$. The crystalline Form I of nicotinamide riboside chloride may also or alternatively be characterized by a solid-state IR spectrum having peaks at 671.7, 1035.6, 1061.8, 1398.9, and 1649.3 cm$^{-1}$±0.2 cm$^{-1}$. In certain instances, the crystalline Form I of nicotinamide riboside chloride may be characterized by a solid-state IR spectrum substantially as shown in FIG. 4. In further instances, the crystalline Form I of nicotinamide riboside chloride may be characterized by a solid-state IR spectrum having peaks substantially as provided in Table 4, below, ±0.2 cm$^{-1}$.

TABLE 4

| IR (cm$^{-1}$) |
|---|
| 3307.91 |
| 3236.09 |
| 3150.27 |
| 2967.14 |
| 1702.35 |
| 1667.56 |
| 1649.34 |
| 1611.33 |
| 1582.94 |
| 1468.53 |
| 1436.77 |
| 1398.92 |
| 1324.43 |
| 1291.92 |
| 1263.29 |
| 1215.24 |
| 1179.00 |
| 1148.84 |
| 1135.31 |
| 1110.95 |
| 1101.18 |
| 1061.82 |
| 1035.62 |
| 986.71 |
| 926.55 |
| 899.63 |
| 852.33 |
| 830.75 |
| 779.75 |
| 760.46 |
| 734.93 |
| 705.48 |
| 671.72 |
| 3307.91 |
| 3236.09 |
| 3150.27 |
| 2967.14 |
| 1702.35 |
| 1667.56 |
| 1649.34 |
| 1611.33 |
| 1582.94 |

TABLE 4-continued

| IR (cm$^{-1}$) |
|---|
| 1468.53 |
| 1436.77 |
| 1398.92 |
| 1324.43 |
| 1291.92 |
| 1263.29 |
| 1215.24 |
| 1179.00 |
| 1148.84 |
| 1135.31 |
| 1110.95 |
| 1101.18 |
| 1061.82 |
| 1035.62 |
| 986.71 |
| 926.55 |
| 899.63 |
| 852.33 |
| 830.75 |
| 779.75 |
| 760.46 |
| 734.93 |
| 705.48 |
| 671.72 |

Preparation of Form II of Crystalline Nicotinamide Riboside Chloride

A mixture was formed comprising methanol, Form I of crystalline nicotinamide riboside chloride as disclosed in U.S. Provisional Application No. 62/028,685, filed Jul. 24, 2014, and five volumes of methanol containing 3.5% water by volume having a temperature of −10° C. The mixture was agitated for at least 12 hours while being held at −10° C., and then the nicotinamide riboside chloride solids were isolated. The isolated methanol-containing wetcake was then charged to 2.5 volumes of cold (−10° C.) acetone. The temperature of the combination was then adjusted to 20-25° C. While the combination was subjected to agitation, water having a temperature of 20-25° C. was added until the mixture contained 3.5% water by volume relative to the volume of acetone. The mixture was then agitated at 20-25° C. for at least 12 hours. The nicotinamide riboside chloride solids were isolated and washed with acetone and 3.5% water by volume. The isolated, washed wetcake was vacuum-dried at 35° C. until dry. The dried material was crystalline Form II of nicotinamide riboside chloride.

The preceding reaction/cooling times were based on plant production of hundreds of kilograms. As those skilled in the art would readily appreciate, many of the times may be reduced when performing the reaction on a smaller scale, without a dramatic effect on the morphology and physical form.

Evaluation of Crystalline Form II of Nicotinamide Riboside Chloride

The DSC thermogram of crystalline Form II of nicotinamide riboside chloride produced a peak at 126.57° C. This can be said to represent a melting point of crystalline Form II of nicotinamide riboside chloride, and is approximately 4° C. above the melting point of Form I.

Scanning Electron Microscopy images of crystalline Form II of nicotinamide riboside chloride were obtained. FIG. 4 depicts a Scanning Electron Microscopy (SEM) image of the presently disclosed form of crystalline nicotinamide riboside chloride.

Instrumentation

X-ray powder diffraction. The X-ray powder diffraction information concerning the crystalline nicotinamide riboside chloride was obtained using PANalytical X-PertPRO Multi-Purpose Diffractometer, model #PY3040. No special sample preparation was required.

SEM. Scanning Electron Microscopy images were obtained using Hitachi FE-SEM model #S-4500. No special sample preparation was required.

Infrared Spectroscopy. Fourier Transform Infrared Spectroscopy (FTIR) spectra were obtained using a Spectrum One™ FTIR instrument with universal Attenuated Total Reflection (Perkin-Elmer, Inc., Waltham, Mass.).

Differential scanning calorimetry (DSC). Thermograms were obtained using a Q2000 Differential Scanning Calorimeter, V24.11, Build 124 (TA Instruments, New Castle, Del.).

What is claimed:

1. A crystalline Form II of nicotinamide riboside chloride

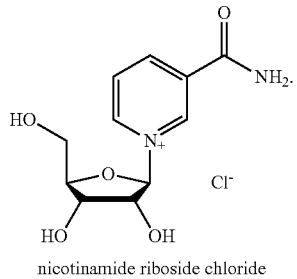

nicotinamide riboside chloride

2. The crystalline Form II according to claim 1 that is characterized by a powder X-ray diffraction pattern having peaks at 21.9, 22.1, and 24.7 degrees two theta±0.2 degrees two theta.

3. The crystalline Form II according to claim 1 that is characterized by a powder X-ray diffraction pattern having peaks at 21.2, 21.9, 22.1, 24.7, and 33.8 degrees two theta±0.2 degrees two theta.

4. The crystalline Form II according to claim 1 that is characterized by a powder X-ray diffraction pattern having peaks at 21.2, 21.9, 22.1, 23.9, 24.7, 29.6, and 33.8 degrees two theta±0.2 degrees two theta.

5. The crystalline Form II according to claim 1 that is characterized by a powder X-ray diffraction pattern having peaks at 10.2, 10.7, 13.8, 21.2, 21.9, 22.1, 23.2, 23.9, 24.7, 29.6, and 33.8 degrees two theta±0.2 degrees two theta.

6. The crystalline Form II according to claim 1 that is characterized by a powder X-ray diffraction pattern substantially as shown in FIG. 1.

7. The crystalline Form II according to claim 1 that is characterized by a powder X-ray diffraction pattern having peaks substantially as shown in Table 1±0.2 degrees two theta.

8. The crystalline Form II according to claim 1 that is characterized by an IR spectrum having peaks at 678.3, 695.6, and 1097.5 $cm^{-1}$±0.2 $cm^{-1}$.

9. The crystalline Form II according to claim 1 that is characterized by an IR spectrum having peaks at 678.3, 695.6, 930.1, 1084.7, and 1097.5 $cm^{-1}$±0.2 $cm^{-1}$.

10. The crystalline Form II according to claim 1 that is characterized by an IR spectrum having peaks at 678.3, 695.6, 930.1, 998.6, 1084.7, 1097.5, and 1412.6 $cm^{-1}$±0.2 $cm^{-1}$.

11. The crystalline Form II according to claim 1 that is characterized by an IR spectrum substantially as shown in FIG. 2.

12. The crystalline Form II according to claim 1 that is characterized by an IR spectrum having peaks substantially as shown in Table 2±0.2 $cm^{-1}$.

13. The crystalline Form II according to claim 1 that is characterized by a differential scanning calorimetry thermogram having a peak at about 126.57° C.

14. The crystalline Form II according to claim 1 wherein said crystalline Form II is anhydrous.

15. A pharmaceutical composition comprising the crystalline Form II according to claim 1 and a pharmaceutically acceptable excipient.

16. A method of producing a pharmaceutical composition comprising combining the crystalline Form II according to claim 1 with a pharmaceutically acceptable excipient.

17. A method comprising administering to a subject the crystalline Form II according to claim 1 or the pharmaceutical composition of claim 15.

18. A method of preparing a crystalline Form II of nicotinamide riboside chloride

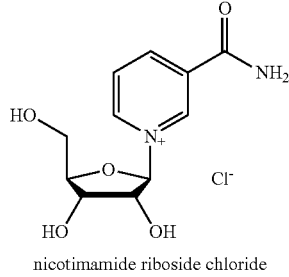

nicotimamide riboside chloride comprising:
  forming a mixture comprising nicotinamide riboside chloride and a polar solvent with hydrogen bonding;
  optionally isolating a wetcake comprising said nicotinamide riboside chloride from said mixture and forming a second mixture comprising said nicotinamide riboside chloride and a further quantity of said polar solvent with hydrogen bonding or a different polar solvent with hydrogen bonding;
  raising the temperature of the mixture or the second mixture;
  and,
  isolating crystalline Form II of nicotinamide riboside chloride from the mixture or the second mixture.

19. The method according to claim 18 wherein said mixture comprises the nicotinamide riboside chloride, the polar solvent with hydrogen bonding, and water.

20. The method according to claim 18 wherein the polar solvent with hydrogen bonding in said mixture is methanol.

21. The method according to claim 18 wherein the polar solvent with hydrogen bonding in said second mixture is acetone.

22. The method according to claim 21 wherein said second mixture further comprises water.

23. The method according to claim 18 wherein said mixture is formed by combining crystalline nicotinamide riboside chloride and said polar solvent with hydrogen bonding.

24. A crystalline Form II of nicotinamide riboside chloride that is prepared according to the method of claim 18.

* * * * *